(12) United States Patent
Polyakov et al.

(10) Patent No.: US 9,233,207 B2
(45) Date of Patent: Jan. 12, 2016

(54) DEVICE FOR ADMINISTERING THERAPEUTIC SUBSTANCES USING A HIGH VELOCITY LIQUID-GAS STREAM

(75) Inventors: Alexander Polyakov, Ramat Hagolan (IL); Yitzhak Yaniv, Ganei Tikva (IL)

(73) Assignee: TAVTECH LTD., Yehud (IL)

( * ) Notice: Subject to any disclaimer, the term of this patent is extended or adjusted under 35 U.S.C. 154(b) by 0 days.

(21) Appl. No.: 14/000,873

(22) PCT Filed: Feb. 20, 2012

(86) PCT No.: PCT/IL2012/050053
§ 371 (c)(1),
(2), (4) Date: Aug. 22, 2013

(87) PCT Pub. No.: WO2012/114337
PCT Pub. Date: Aug. 30, 2012

(65) Prior Publication Data
US 2013/0331816 A1    Dec. 12, 2013

Related U.S. Application Data

(60) Provisional application No. 61/457,306, filed on Feb. 22, 2011.

(51) Int. Cl.
*A61M 5/30* (2006.01)
*A61M 5/20* (2006.01)
A61B 17/54 (2006.01)
A61B 17/00 (2006.01)
A61C 19/06 (2006.01)

(52) U.S. Cl.
CPC ............. *A61M 5/30* (2013.01); *A61M 5/2053* (2013.01); *A61B 17/545* (2013.01); *A61B 2017/00761* (2013.01); *A61C 19/063* (2013.01); *A61M 5/204* (2013.01); *A61M 5/2066* (2013.01)

(58) Field of Classification Search
CPC ...... A61M 5/30; A61M 5/204; A61M 5/2053
USPC .................................. 604/24, 68, 70, 71, 72
See application file for complete search history.

(56) References Cited

U.S. PATENT DOCUMENTS

| | | | |
|---|---|---|---|
| 3,908,651 A | | 9/1975 | Fudge |
| 4,403,986 A | * | 9/1983 | Dettbarn et al. ................. 604/70 |
| 4,560,377 A | | 12/1985 | Geat |
| 7,601,137 B2 | * | 10/2009 | Meijering et al. .............. 604/68 |
| 7,699,803 B2 | * | 4/2010 | Nayak et al. .................... 604/72 |
| 8,057,426 B2 | * | 11/2011 | Nayak et al. .................... 604/82 |
| 2005/0085767 A1 | * | 4/2005 | Menassa ......................... 604/68 |
| 2009/0036824 A1 | | 2/2009 | Tavger |

* cited by examiner

*Primary Examiner* — Theodore Stigell
*Assistant Examiner* — Benjamin Koo
(74) *Attorney, Agent, or Firm* — JMB Davis Ben-David

(57) ABSTRACT

A device, system and method for treatment of tissue by direct application thereto of therapeutic substances in the form of a stream of therapeutic droplets carried in a high velocity gas. The high velocity gas is produced by accelerating a flow of gas through at least one gas discharge nozzle. At least one flow of therapeutic liquid is introduced into the high velocity gas through at least one liquid discharge nozzle, thereby fragmenting the at least one flow of therapeutic liquid into a stream of therapeutic droplets. The stream is accelerated to a velocity similar to the velocity of the gas discharge flow. The accelerated therapeutic droplet stream is then applied to a tissue mass for therapeutic treatment. The therapeutic substances are provided by containers mounted directly on the device. The containers contain predefined dosages and/or concentrations of the therapeutic substances.

21 Claims, 13 Drawing Sheets

DEVICE FOR ADMINISTERING THERAPEUTIC SUBSTANCES USING A HIGH VELOCITY LIQUID-GAS STREAM

CROSS REFERENCE TO RELATED APPLICATION

This is the U.S. National Stage of International Application No. PCT/IL2012/050053, filed Feb. 20, 2012, which was published in English under PCT Article 21(2), which in turn claims the benefit of U.S. provisional patent application Ser. No. 61/457,306, filed Feb. 22, 2011, titled "A Device For Administering Therapeutic Substances Using a High Velocity Liquid-Gas Stream", which is incorporated herein by reference in its entirety.

FIELD OF THE INVENTION

The present invention relates, generally, to devices for administering therapeutic substances in predefined dosages and concentrations, and, more specifically, to devices for applying a high velocity therapeutic liquid-gas stream for administering such substances to body tissue in predefined dosages and concentrations.

BACKGROUND OF THE INVENTION

Devices for dermal abrasion of exposed in vivo tissue are known in the art. One such device is described in International Publication Number WO 2005/065032, "A High Velocity Liquid-Gas Mist Tissue Abrasion Device", included herein by reference. This document also provides a general overview of the prior art of dermal abrasion and dermal abrasion devices.

Disclosed in the above referenced document is a device for dermal abrasion employing a high-velocity liquid-gas streaming mist. The disclosed device is particularly successful in overcoming the difficulty of stagnant boundary layers. When a fluid stream is employed to irrigate a tissue surface, a boundary layer is formed which is characterized by having a fluid velocity which decreases sharply adjacent to the flow surface, being virtually zero at the tissue surface. As a result, particles which are smaller than the thickness of the boundary layer of the fluid stream are often difficult or impossible to remove. The smallest particles in the boundary layer exhibit a drag resistance of a magnitude sufficient for these particles to remain attached to the surface and to resist being swept away by the fluid stream. The device disclosed in the above referenced document overcomes this difficulty, its liquid-gas streaming mist producing a boundary layer of minimal to negligible thickness.

However, neither the device disclosed in the above mentioned document nor other prior art devices discussed therein provide for a construction designed to easily allow treatment of abraded tissue with therapeutic substances in predefined dosages and/or concentrations. Additionally, the above mentioned device and other prior art devices require relatively large liquid and gas sources, suitable for use with a plurality of patients. These sources are positioned distant from the device necessitating the use of connecting tubes which inter alia impede use, especially one-hand use, of the devices.

DEFINITIONS

In the discussion herein below, the term "distal" refers to the position on the devices discussed herein furthest from the user that is the portion closest to the nozzle arrangement of the devices. The term "proximal" refers to the position on the devices closest to the user that is the portion furthest from the nozzle arrangement of the devices.

The terms "cleanse", "cleaning" and variants thereof in the discussion herein below, refers to the removal of solid contaminants, such as fibers, dust, sand particles, and the like, as well as the removal of organic matter, such as pus, fats, and the like from the surface of tissue being cleaned and/or being treated with therapeutic substances. The term "cleanse" includes lavage of hollow organs of the body.

The term "tissue" as used herein can refer to either human or animal tissue.

SUMMARY OF THE INVENTION

The present invention provides a device, system and a method for treatment of tissue by direct application thereto of desired therapeutic substances in the form of a stream of therapeutic droplets carried in a high velocity gas. The present invention provides a housing for a device that does not require liquid and therapeutic substance sources to be positioned distant from the housing. Connecting elements such as tubing are therefore minimized and operation of the device made easier. Additionally, dosage and concentration control of the therapeutic substances is simplified.

In a first aspect of the present invention, there is provided a device for administering a therapeutic substance to tissue for use with a pressurized gas source, and comprising: a) a housing having a liquid inlet port; b) a gas inlet port connected to the pressurized gas source; c) one or more therapeutic substance supply assemblies mounted onto the housing, each therapeutic substance supply assembly comprising one or more container connectors, each connector configured for receiving a container containing a predefined quantity or concentration of liquid therapeutic substance; and d) a stream jet delivery nozzle arrangement in fluid flow communication with the gas inlet port and in fluid flow communication with the one or more therapeutic substance supply assemblies. The liquid therapeutic substance is discharged from the stream jet delivery nozzle arrangement into an elevated velocity flow of gas, the latter also discharged from the delivery nozzle arrangement.

In some embodiments of the device, the therapeutic substance supply assembly comprises one or more container connectors, one or more liquid conduit and an assembly base. The one or more container connectors are in liquid supply communication with the one or more conduit and with the assembly base. The assembly base is an at least partially hollow integral mounting and connector member for mounting the therapeutic substance supply assembly onto the housing. The assembly base is formed so that it includes a conduit in fluid flow communication with the one or more liquid conduits of the assembly and the liquid inlet port thereby facilitating fluid flow between them.

In yet another embodiment of the device, the therapeutic substance supply assembly further comprises one or more connection fittings and optionally one or more valves. The one or more connection fittings and the one or more valves are in fluid flow communication with both the one or more container connectors and the one or more liquid conduits of the assembly. In some instances, the connection fittings may be luer locks and the valves may be stopcock valves.

In other embodiments of the device, the therapeutic substance supply assembly sequentially comprises a container connector, a connection fitting, an optional valve, a liquid conduit and an assembly base, all of the elements constructed and adapted to be in fluid flow communication with the proceeding element in the sequence when liquid flows out of a container received in the container connector toward the assembly base. It is to be understood that the elements listed above may be arranged in a different sequence. But in such an alternate sequence, all of the elements are again constructed and adapted to be in fluid flow communication with the proceeding element in the sequence when liquid flows out of a container received in the container connector toward the assembly base.

In some embodiments of the device, the liquid therapeutic substance is brought to the liquid inlet port from the therapeutic substance supply assembly through a tube in fluid flow communication with the assembly base.

In yet other embodiments of the device, the one or more container connector includes a puncturing element for piercing a cap of the container containing a liquid therapeutic substance thereby allowing the therapeutic substance to flow from the container either under pressure when the therapeutic substance is packaged in the container under pressure or by gravity.

In other embodiments of the device, the liquid inlet port is in fluid flow communication with the therapeutic substance supply assembly and also in fluid communication with the stream jet delivery nozzle arrangement.

In still other embodiments of the device, the device further comprises one or more valves positioned on the therapeutic substance supply assembly for controlling fluid flow through the assembly.

In other embodiments of the device, the stream jet delivery nozzle arrangement comprises: i) one or more gas discharge nozzles arranged to receive a flow of pressurized gas from the gas inlet port and configured to accelerate the flow of gas so as to discharge it at an elevated velocity; and ii) one or more liquid discharge nozzles arranged to receive a flow of liquid therapeutic substance from the one or more therapeutic substance supply assemblies and operative to discharge the flow of therapeutic substance into the elevated velocity flow of gas, thereby to accelerate the velocity of the discharged liquid therapeutic substance as a stream of accelerated therapeutic droplets and to discharge the stream of accelerated therapeutic droplets towards a tissue mass for treatment by the therapeutic substance.

In another embodiment of the device, the housing has an aperture formed on its long tubular side and further comprises a liquid communication tube extending to the aperture. The assembly base is an at least partially hollow integral mounting and connector member for mounting said therapeutic substance supply assembly onto said housing, further having formed therein a conduit in fluid flow communication with the one or more liquid conduits of said assembly and said liquid communication tube of said housing for facilitating fluid flow therebetween.

In another aspect of the invention, there is provided a system for administering a therapeutic substance to tissue, which comprises: a) a pressurized gas source; b) one or more containers containing a predefined quantity or concentration of a liquid therapeutic substance; and c) a device which comprises: (i) a housing having a liquid inlet port; (ii) a gas inlet port connected to the pressurized gas source; (iii) one or more therapeutic substance supply assemblies mounted on the housing. Each therapeutic substance supply assembly includes one or more container connectors configured for receiving one of the one or more containers containing a predefined quantity or concentration of a liquid therapeutic substance; and (iv) a stream jet delivery nozzle arrangement in fluid flow communication with the gas inlet port and the therapeutic substance supply assembly. The liquid therapeutic substance is discharged from the nozzle arrangement into an elevated velocity flow of gas also discharged from the delivery nozzle arrangement.

In some embodiments of the system, the therapeutic substance supply assembly comprises one or more container connectors, one or more liquid conduits and an assembly base. The one or more container connectors are in liquid supply communication with the one or more conduits and with the assembly base. The assembly base is an at least partially hollow integral mounting and connector member for mounting the therapeutic substance supply assembly onto the housing. The base includes a conduit in fluid flow communication with the one or more liquid conduits of the assembly and the liquid inlet port for facilitating fluid flow therebetween.

In another embodiment of the system, the therapeutic substance supply assembly further comprises one or more connection fittings and optionally one or more valves. The one or more connection fittings and the one or more valves are in fluid flow communication with the one or more container connectors and the one or more liquid conduits.

In still other embodiments of the system, the therapeutic substance supply assembly sequentially comprises a container connector, a connector fitting, an optional valve, a liquid conduit and an assembly base. All of the elements are constructed and adapted to be in fluid flow communication with the proceeding element in the sequence when liquid flows out of a container received in the container connector toward the assembly base.

In another embodiment of the system, the liquid therapeutic substance is brought to the liquid inlet port from the therapeutic substance supply assembly through a tube in fluid flow communication with the assembly base.

In yet another embodiment of the system, the one or more container connectors each include a puncturing element for piercing a cap of the one or more containers of the liquid therapeutic substance. This allows the therapeutic substance to flow from the one or more containers either by gravity or under pressure when the therapeutic substance is packaged in the container under pressure.

In a further embodiment of the system, the therapeutic substance supply assembly further comprises one or more valves positioned thereon for controlling fluid flow through the assembly.

In another embodiment of the system, the liquid inlet port is in fluid flow communication with the therapeutic substance supply assembly and also in fluid flow communication with the stream jet delivery nozzle arrangement.

In yet another embodiment of the system, the stream jet delivery nozzle comprises: 1) one or more gas discharge nozzles arranged to receive a flow of pressurized gas from the gas inlet port and configured to accelerate the flow of gas so as to discharge it at an elevated velocity; and 2) one or more liquid discharge nozzles arranged to receive a flow of therapeutic substance from the one or more therapeutic substance supply assemblies and operative to discharge the flow of therapeutic substance into the elevated velocity flow of gas, thereby accelerating the velocity of the discharged liquid therapeutic substance as a stream of accelerated therapeutic droplets and discharging the stream of accelerated therapeutic droplets towards a tissue mass for treatment by the therapeutic substance.

In yet another embodiment of the system, the housing of the device has an aperture formed on its long tubular side and further comprises a liquid communication tube extending to the aperture. The assembly base of the therapeutic substance supply assembly is an at least partially hollow integral mounting and connector member for mounting the therapeutic substance supply assembly onto the housing and further has formed therein a conduit in fluid flow communication with the one or more liquid conduits of the assembly and the liquid communication tube of the housing, thereby facilitating fluid flow therebetween.

In a third aspect of the present invention, there is provided a method for administering a liquid therapeutic substance to tissue which comprises the following steps: (a) providing one or more containers containing a predefined quantity or concentration of a liquid therapeutic substance; (b) accelerating a flow of gas through one or more gas discharge nozzles so as to provide a gas discharge flow at an elevated velocity; (c) introducing into the elevated velocity gas discharge flow one or more flows of the liquid therapeutic substance from the one or more containers having a predefined dosage and/or concentration through one or more liquid discharge nozzles, thereby to fragment the flow of liquid therapeutic substance into a stream of therapeutic droplets, and to accelerate the stream to a velocity similar to the velocity of the gas discharge flow; and (d) exposing the tissue mass to the accelerated therapeutic droplet stream for therapeutic treatment thereby.

In an embodiment of the method, in the step of introducing, the one or more flows of liquid therapeutic substance is a flow of saline solution; and the step of introducing further includes the step of supplying to the one or more flows of saline solution a predetermined flow of the one or more additional therapeutic substances, thereby producing a mixed flow of therapeutic liquid having a predefined concentration of the one or more additional therapeutic substances. In instances of this embodiment, the step of supplying is performed at preselected times for preselected time intervals.

In another embodiment of the method, in the step of introducing, the one or more flows of therapeutic liquid is at least two flows of therapeutic liquid, wherein a first flow of therapeutic liquid is a flow of saline solution and one or more additional flows of therapeutic liquid is a predetermined flow of the one or more additional therapeutic substances, thereby producing a stream of therapeutic droplets containing a predefined concentration and/or dosage of the one or more additional therapeutic substances.

In still another embodiment of the method, in the step of introducing, the one or more flows of therapeutic liquid is introduced at preselected times for preselected time intervals.

In embodiments of the method, the liquid therapeutic substance includes a liquid selected from a group which consists of: saline solution, a medication, a nutrient, a moisturizer, and a mixture of any of the aforementioned therapeutic substances.

BRIEF DESCRIPTION OF THE DRAWINGS

The present invention will be more fully understood and its features and advantages will become apparent to those skilled in the art by reference to the ensuing description, taken in conjunction with the accompanying drawings, in which.

DETAILED DESCRIPTION OF THE INVENTION

Figure 1:
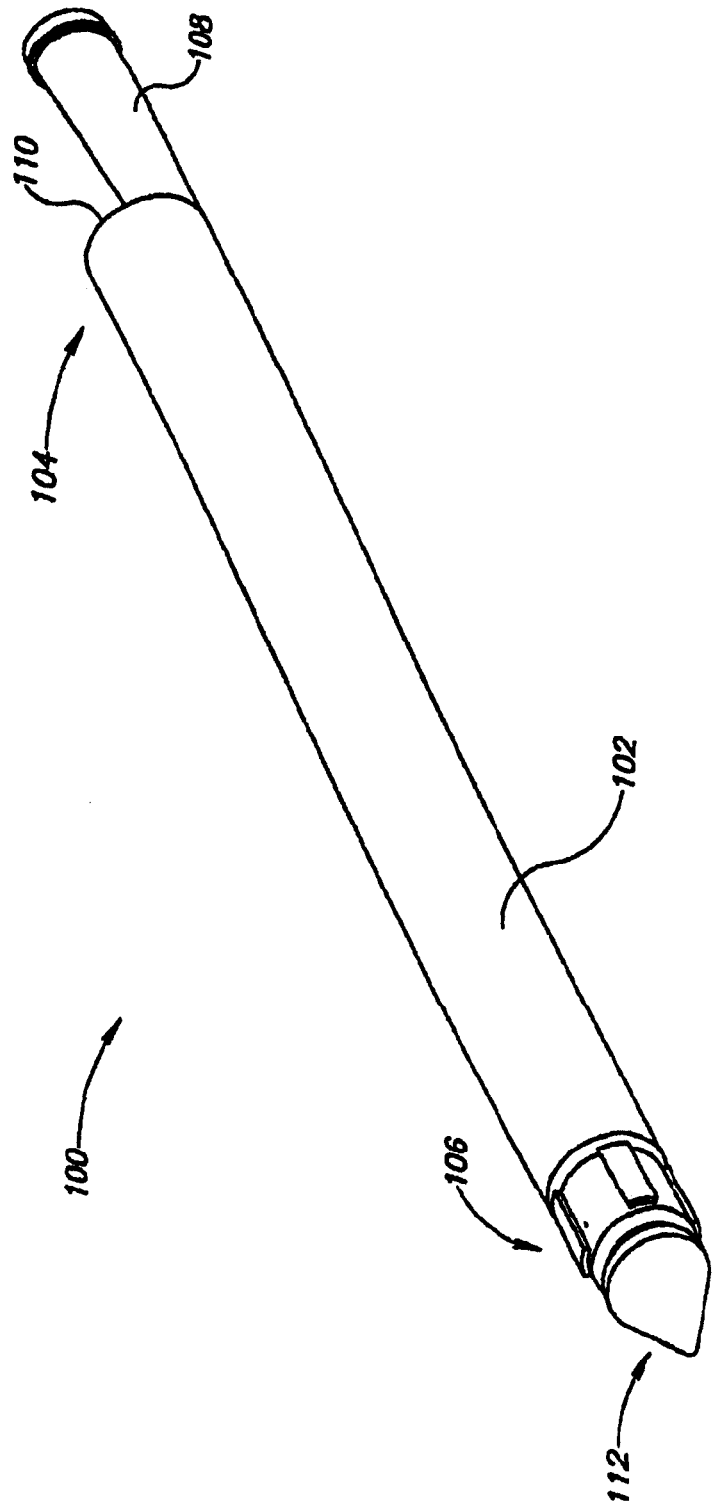
FIG. 1 is a perspective view of a prior art device for administering therapeutic substances to tissue.

The present invention relates to a device for administering therapeutic substances to tissue by directing a liquid-gas stream of droplets containing one or more therapeutic substances. The device of the present invention comprises two elements, a housing and a stream jet nozzle arrangement, the latter mechanically connected to the housing.

The liquid-gas stream consists of one or more therapeutic liquids provided at a high velocity, generally within the range of sub-sonic to super-sonic. To achieve these high velocities, gas is discharged from a device containing a stream jet nozzle arrangement, the arrangement containing one or more converging-diverging gas nozzles configured to accelerate the flow of gas so as to discharge it at an elevated velocity. A low rate of flow of therapeutic liquid is discharged into the elevated velocity flow of gas, thereby accelerating the discharged therapeutic liquid as a therapeutic stream of accelerated droplets. The volumetric rate of flow of therapeutic liquid from the device is relatively low, thereby essentially preventing the formation of a virtually stagnant liquid boundary layer on the surface of the tissue to which the therapeutic substances is being administered.

The housing of the device is in fluid flow communication with one or more containers containing one or more therapeutic substances. The therapeutic substances may be provided in bottles, vials, ampoules, or any other suitable containers. The containers are removably affixed to and positioned on the housing via a therapeutic substance supply assembly as described below and shown in FIGS. 8A-8G. The containers containing the therapeutic substances are generally single-use containers which contain predefined quantities and/or concentrations of therapeutic substances.

When the therapeutic liquid administered by the present invention is saline solution, the invention can be employed to clean a tissue surface. Subsequently, additional therapeutic substances, such as medications, nutrients, moisturizers or colorants may be administered. These therapeutic substances may be in liquid, emulsion or soluble powder form. This allows for more efficient dosing of the therapeutic substances, since, as will be appreciated by persons skilled in the art, the substances removed by cleaning would, if left in place, likely impede application and/or absorption of the desired therapeutic substances to the tissue undergoing therapeutic treatment.

The therapeutic substance supply assembly attached to the substantially tubular shaped housing of the present invention may include control valves operative for introducing into the device of the present invention a mixed flow of saline solution and other therapeutic substances. The valves can be used to obtain a desired concentration therein which can further be controlled, typically but without limiting the invention, by the operator during operation, to produce the mixed flow at specified times and for specified intervals. The device of the present invention would then accordingly produce a mixed therapeutic stream as desired and needed. Thus, as described above, a tissue surface could first be cleaned by saline solution and then dosed therapeutically with a medication solution when it is ready to optimally receive the dosage.

In an alternative embodiment of the present invention, instead of one mixed flow as mentioned hereinabove, the device of the present invention may be controlled and used to produce a number of therapeutic liquid flows for discharge into the elevated velocity gas flow. The therapeutic substances may also be turned on and off at specified times and for specified intervals. This arrangement also produces a mixed therapeutic stream as desired and needed. For example, the present invention can be used to treat a human scalp even where hair is present. First, the device provides an accelerated saline stream to clean the scalp of extraneous material, excess oils, and dead sloughed off epidermal tissue such as is known to produce dandruff. Then a moisturizing, nutrient, anti-dandruff, or anti-hair loss therapeutic substance is included in the accelerated stream to apply the desired therapeutic treatment to the scalp.

It should further be noted that the present invention is capable of applying the therapeutic substance to the desired tissue both topically and subcutaneously. Investigations employing prototype versions of the present invention have shown that the accelerated therapeutic stream produced thereby will, for suitable droplet flow velocities and time of exposure of the tissue to the droplet flow, penetrate the tissue surface. This capacity of non-invasive subcutaneous treatment and dosage is a further advantage of the present invention.

It is contemplated that the present invention can also be used in lavage of hollow organs of the body.

The discussion in conjunction with FIGS. 1-7 which follows is directed to an exemplary prior art stream jet delivery nozzle arrangement for accelerating a liquid/gas stream in the device of the present invention. In addition to the stream jet delivery nozzle arrangement shown in FIGS. 1-7, other jet delivery nozzle arrangements known in the art may also be used. The housing and control elements described and shown in FIGS. 1-7 are not the housing and control elements envisioned for use with the device of the present invention. The housings and control elements of the device of the present invention are described in conjunction with and shown in FIGS. 8A-8G.

Figure 2:
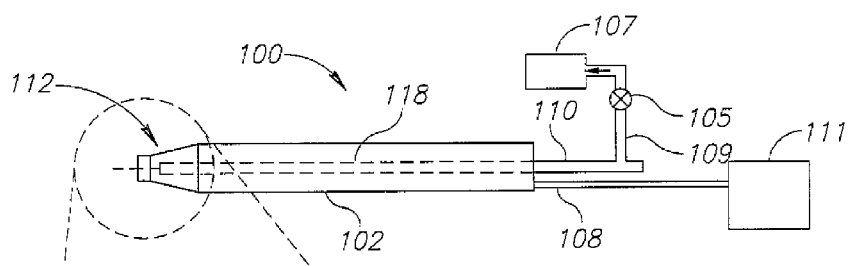
FIG. 2 is a schematic side view of the prior art device of FIG. 1.

With reference to FIGS. 1 and 2, there is seen a device, referenced generally 100, for applying a high velocity liquid-gas therapeutic stream to tissue for therapeutic treatment thereof. Alternatively, the velocity of the stream may be regulated so as to merely provide cleansing of the tissue. Device 100 includes a housing portion referenced 102 having a generally tubular configuration, and having proximal and distal ends, referenced generally 104 and 106, respectively. A gas inlet port, referenced 108, and a liquid inlet port, referenced 110, are provided at proximal end 104, and a stream jet delivery nozzle arrangement referenced generally 112, is provided at distal end 106.

In FIG. 2, there is additionally shown, in schematic form, a therapeutic liquid inlet port 109 connecting pressurized therapeutic liquid source 107 via flow control element 105 to liquid inlet port 110 to allow production of a mixed flow of therapeutic liquid. It should be noted that the present arrangement producing one mixed therapeutic liquid flow is only shown by way of example, and that multiple therapeutic liquid flows, as well as control of the time of application of different therapeutic liquid flows are also contemplated as being part of the discussion herein.

Figure 3:
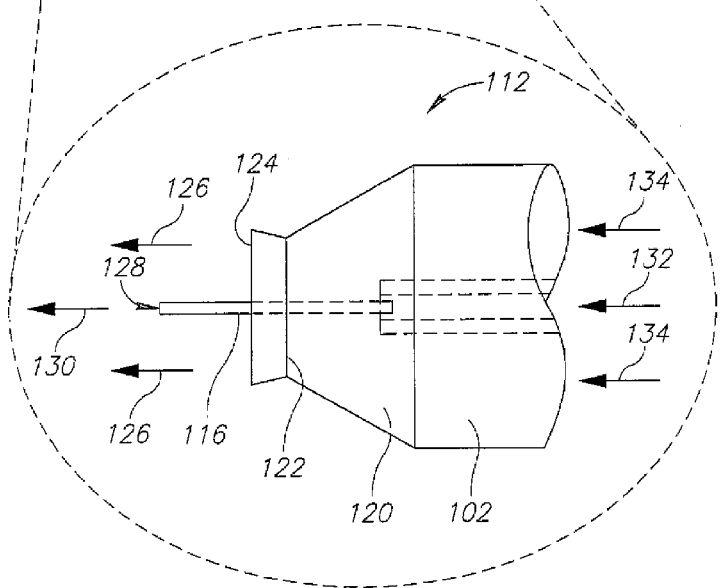
FIGS. 3 and 4 are enlarged schematic and graphical representations, respectively, of a delivery nozzle arrangement of the prior art device seen in FIGS. 1 and 2.
Figure 4:
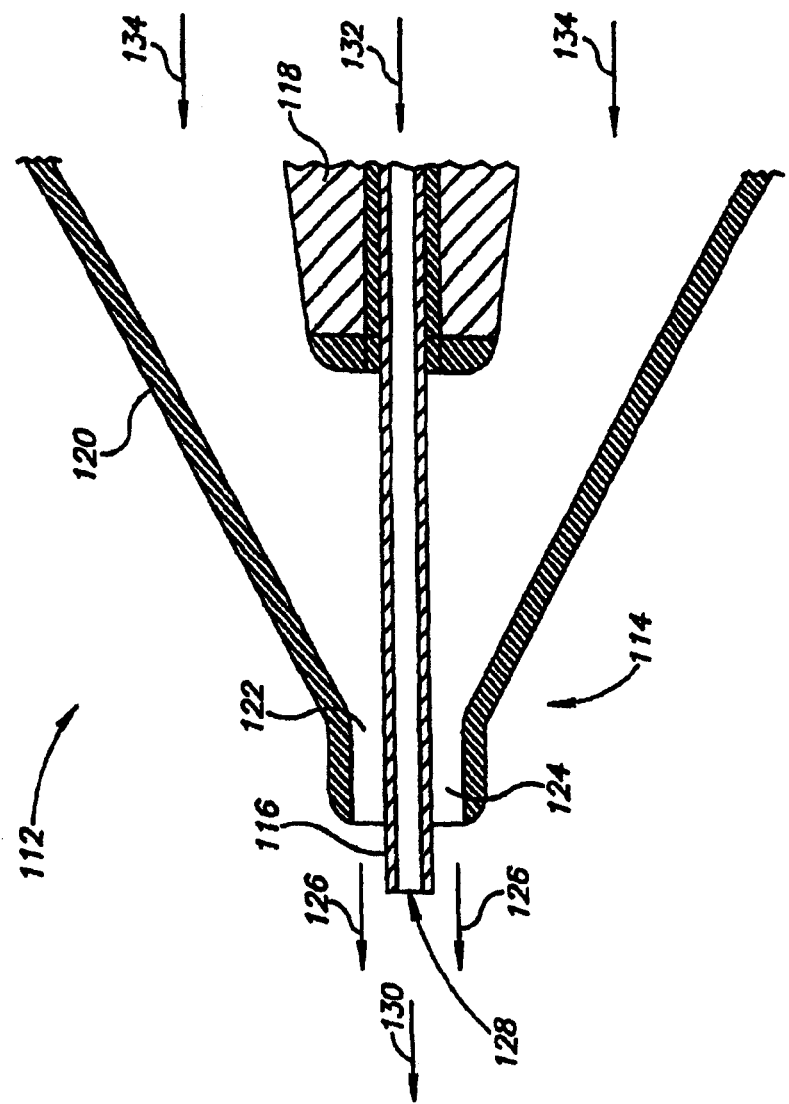

Referring now to FIGS. 3 and 4 in conjunction with FIG. 2, there are seen schematic and graphical cross-sectional views of nozzle arrangement 112 of device 100. Nozzle arrangement 112 includes a gas discharge nozzle referenced generally 114 and, disposed generally concentrically there-within, is a liquid discharge nozzle referenced 116. Liquid inlet port 110 (FIG. 2) is connected in fluid flow communication with liquid discharge nozzle 116 by means of a liquid communication tube referenced 118, disposed generally concentrically within tubular housing portion 102 (FIGS. 2 and 3).

Pressurized gas supplied from a pressurized gas source (not shown) enters device 100 through gas inlet port 108 (FIG. 2) and passes along and within tubular housing portion 102 as indicated by arrows 134, so as to discharge through gas discharge nozzle 114. Gas discharge nozzle 114 is generally configured having, in flow succession, a converging portion referenced 120, a throat portion referenced 122 and a diverging discharge portion referenced 124. The pressurized gas discharging from nozzle 114, as indicated by arrows 126, undergoes a rapid and substantial reduction in pressure to atmospheric pressure and a substantial acceleration to a high velocity, within the range of subsonic to supersonic velocity and specifically to a supersonic velocity. Gas discharge nozzle 114 is configured such that the discharging gas has an average cone angle of less than 10 degrees; that is, providing a substantially parallel gas flow.

Liquid, including therapeutic substances, from one or more pressurized therapeutic liquid sources (not shown) enters device 100 through liquid inlet port 110 (FIG. 2) and passes, as indicated by arrow 132, through liquid communication tube 118 (FIGS. 2 and 4). In turn, at distal end 106, therapeutic liquid is discharged through an opening referenced 128 in the distal end of liquid discharge nozzle 116 into the discharging flow 126 of gas, the therapeutic liquid flow being indicated by arrow 130.

It will be appreciated by persons skilled in the art that, as the pressurized discharging gas emerges 126 from gas discharge nozzle 114 into the atmosphere, it undergoes a rapid drop in pressure to atmospheric pressure. The sudden pressure drop results in a substantial acceleration of the velocity of the discharging gas flow that approximates or even exceeds the velocity of sound and results in the production of a shock wave. The effect of the shock wave is to atomize the therapeutic liquid discharging from liquid discharge nozzle 116 into the flow of gas as a stream of therapeutic liquid droplets 130, such that there is obtained a relatively narrow jet of therapeutic liquid droplets in a high velocity gas flow 126.

Further, by way of example, the proportion of liquid flow to gas flow is extremely low due to the relatively high gas pressure of about 100 psi and low liquid pressure of about 2 psi, as well as the relatively large internal diameter of gas discharge nozzle 114 (about 0.5 mm) compared to a small internal diameter (about 0.09 mm) of liquid discharge nozzle 116. Consequently, little liquid tends to accumulate at the site to be cleaned or treated with one or more therapeutic substances. Furthermore, the relatively high gas flow has the effect of dispersing any accumulated liquid. When using a jet utilizing only liquid for cleansing, the liquid tends to accumulate on the tissue surface resulting in formation of a virtually stagnant liquid boundary layer close to and in contact with the surface, thereby reducing the effectiveness of cleansing. The very thin to negligible layer of liquid produced on the tissue surface by the above described nozzle arrangement allows more efficient dosage of additional therapeutic substances to the tissue surface, including the possibility of subcutaneous application of the therapeutic substances.

Figure 5:
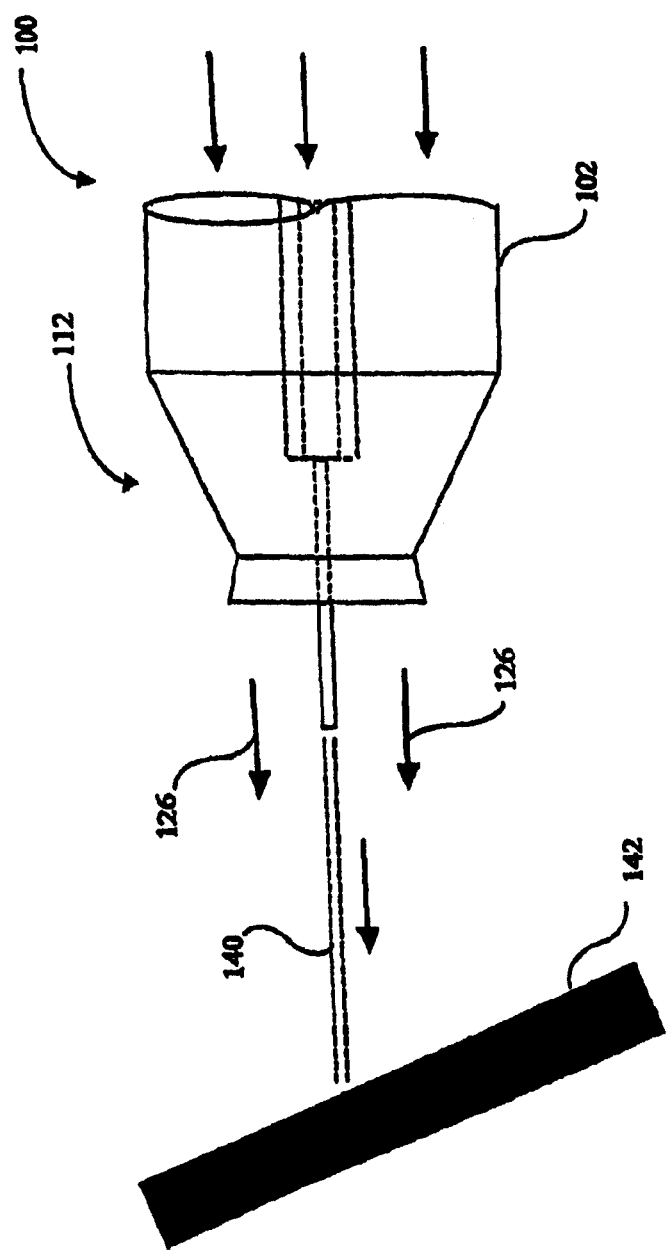
FIG. 5 is a schematic view of a flow of stream droplets discharging from the prior art delivery nozzle arrangement as seen in FIG. 4 against a surface to which therapeutic substances are to be administered.

Referring now to FIG. 5, there is seen a high velocity flow of therapeutic liquid droplets referenced 140 discharging, in a high velocity gas flow 126, from nozzle arrangement 112 against a tissue surface referenced 142 to be cleaned and/or treated with therapeutic substances. Device 100 is held in the hand of a user by housing portion 102.

Figure 6:
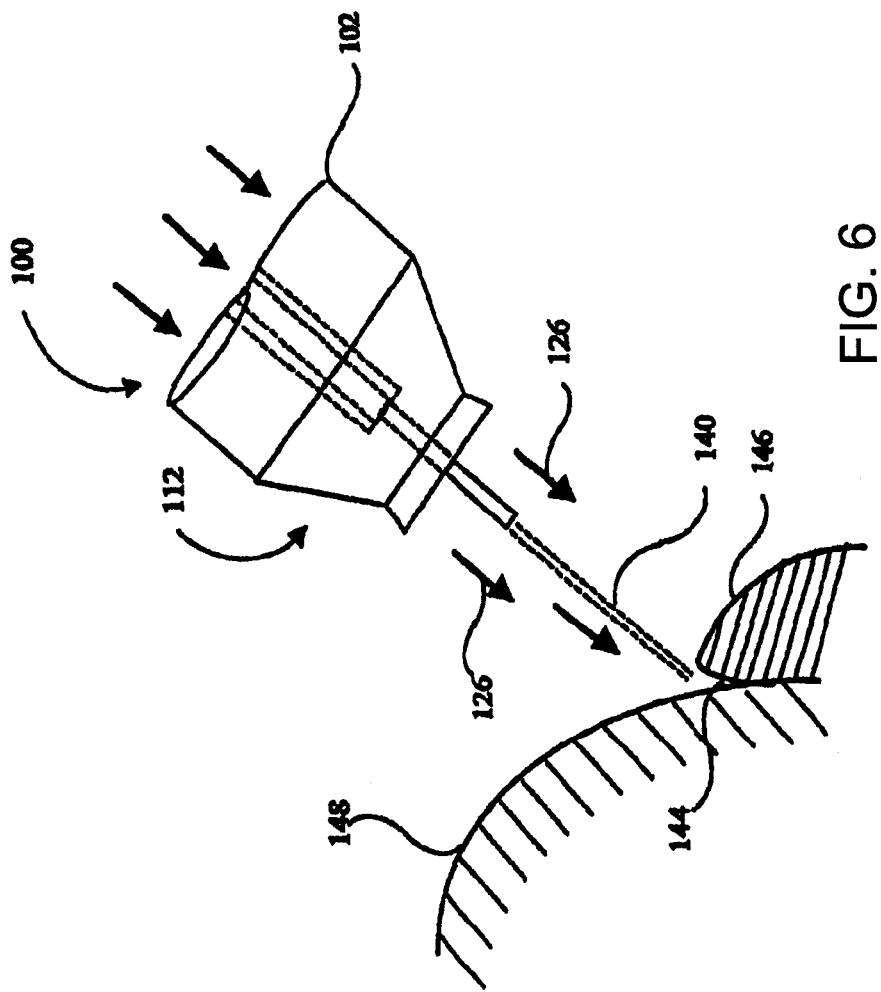
FIG. 6 is a schematic view of a flow of stream droplets discharging from the prior art delivery nozzle arrangement seen in FIG. 4 into a periodontal pocket.

Referring now to FIG. 6, there is seen a flow of therapeutic liquid droplets 140 discharging, in a high velocity gas flow 126, from nozzle arrangement 112 of device 100 into a periodontal pocket referenced 144 disposed between a gum referenced 146 and a tooth wall referenced 148. Device 100 is held in the hand of a user by housing portion 102. This procedure is especially effective for cleansing periodontal pockets, subsequent to a dental descaling treatment, so as to remove plaque and calculus debris as well as bacteria and the toxins produced by the bacteria, which otherwise lead to mechanical irritation and inflammation of the gingiva. Device 100 can further be used to apply desired dental therapeutic substances, such as antibiotics or anesthetics to the dental pocket.

Figure 7:
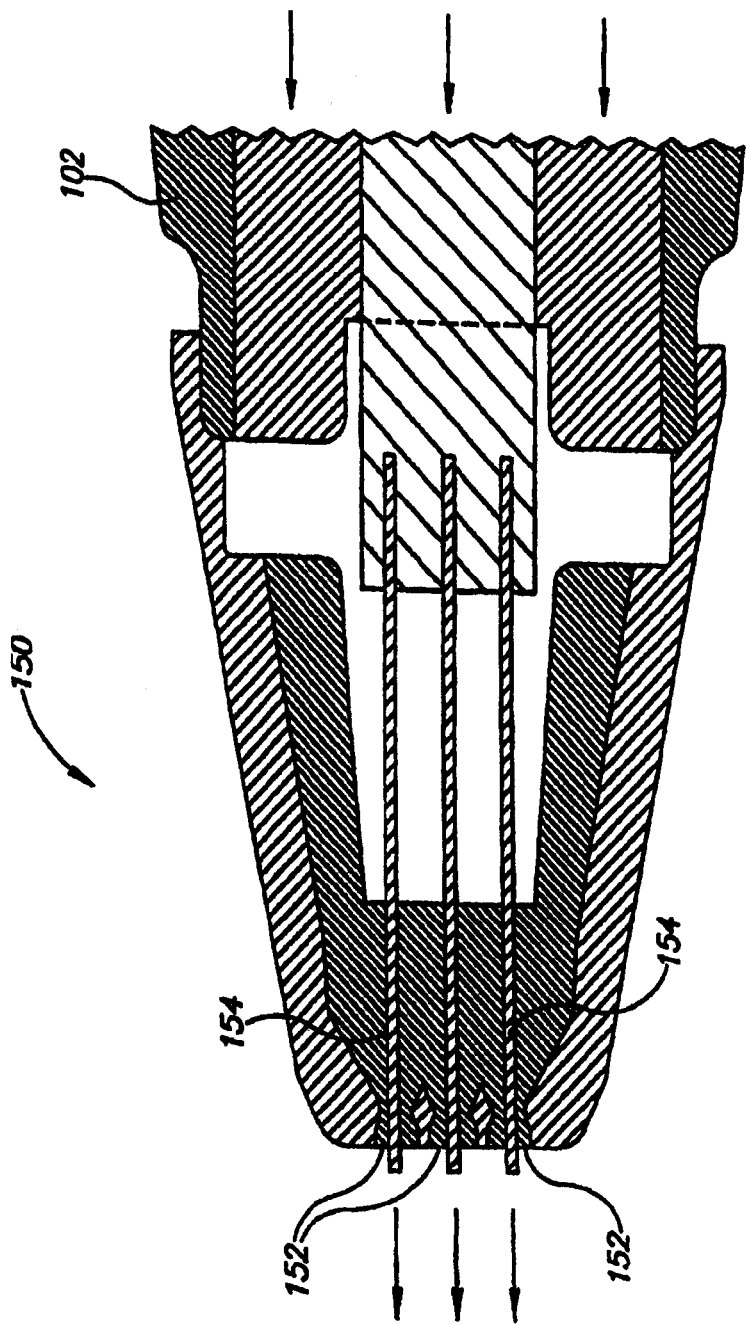
FIG. 7 is a schematic view of a prior art nozzle arrangement having multiple gas and liquid discharge nozzles.

Referring now to FIG. 7, there is seen, according to an alternative construction of the above described device, a cross-sectional view of a device (not shown) having a housing portion 102 and a multiple nozzle arrangement referenced generally 150. Nozzle arrangement 150 is configured having multiple gas discharge nozzles referenced 152 and multiple therapeutic liquid discharge nozzles referenced 154 disposed generally concentrically within each gas nozzle 152 and projecting there-beyond. Such a multiple nozzle arrangement 150 facilitates increasing the rate of tissue cleaning, in the event that the system is used for this purpose. Additionally, the present configuration supports multiple therapeutic liquid flows, which may be individually controlled.

Figure 8A:
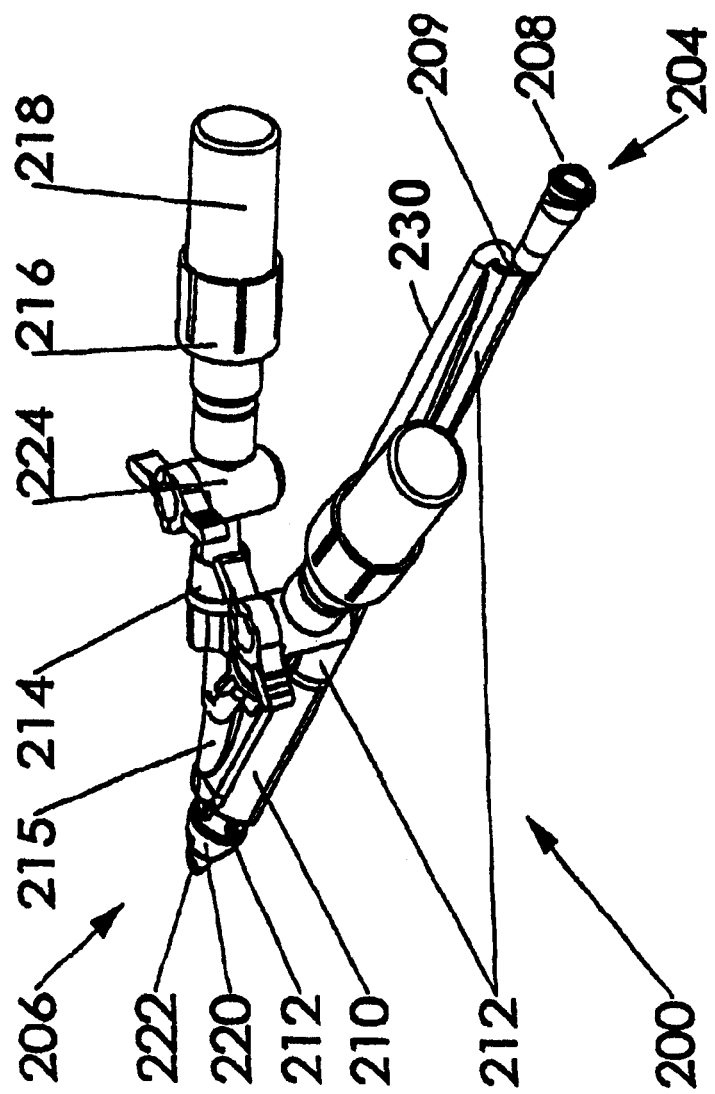
FIGS. 8A-8C are perspective, side and top views, respectively, of a device for administering therapeutic substances to tissue constructed and operative in accordance with an embodiment of the present invention.
Figure 8B:
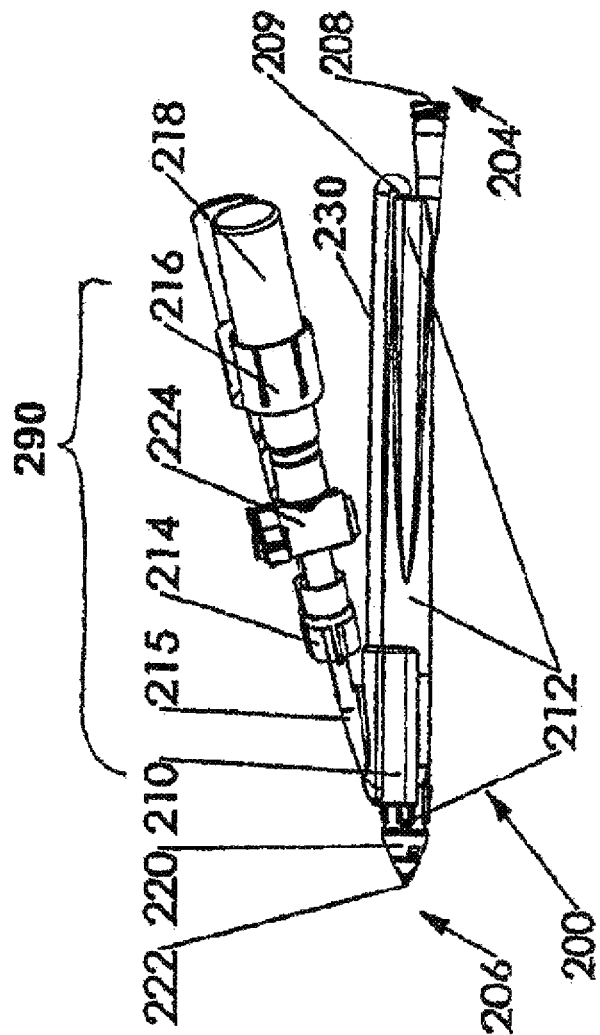
Figure 8C:
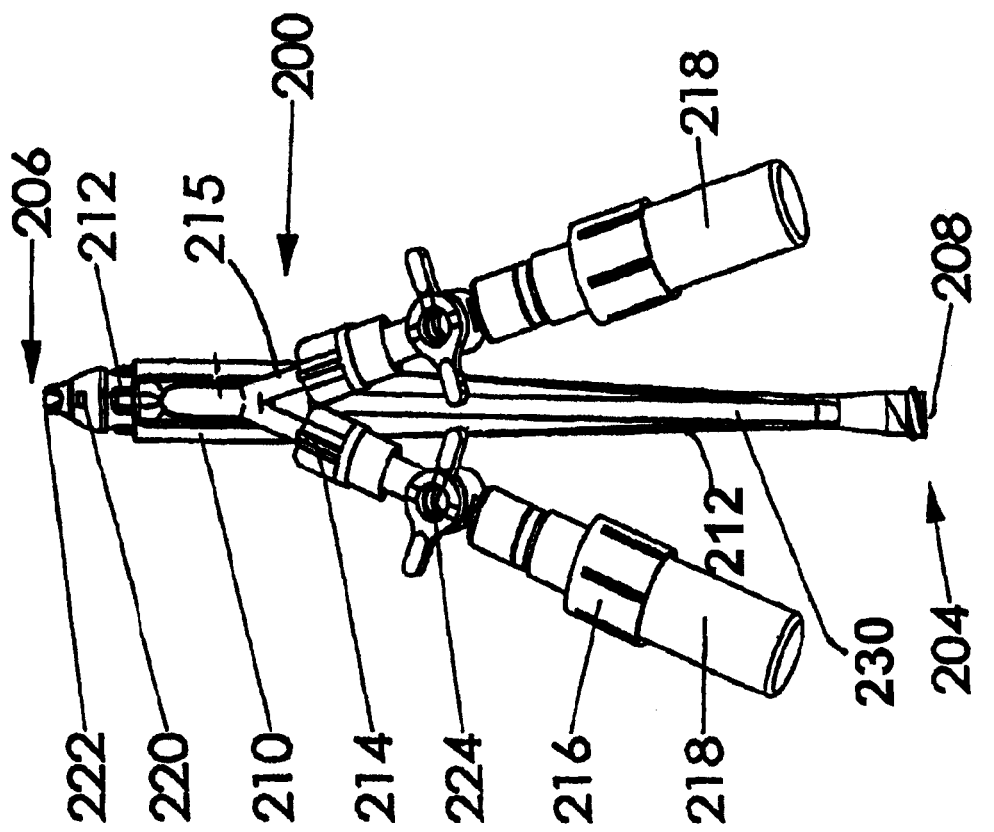

Referring now to FIGS. 8A-8C, there is seen, according to an embodiment of the present invention, a perspective, a side and a top view, respectively, of a device 200 designed to provide one or more (in the Figures one or two) therapeutic substances in predefined dosages and/or concentrations to a patient being treated using the present invention. Without intending to limit the invention, therapeutic substances which may be used include saline solutions, medicaments, nutrients, moisturizers or mixtures of any of these. The housing and control elements in FIGS. 8A-8C (as well as those in FIGS. 8D-8G discussed below) are different from the housing and control elements shown in FIGS. 1 and 2.

Nozzle arrangement 220, discharge nozzles 222 and hand piece housing portion 212 are constructed and configured substantially as described herein above and shown in FIGS. 1-7. Accordingly, description of these elements, their construction and their operation will not necessarily be repeated with respect to the embodiments of the invention presented and discussed in conjunction with FIGS. 8A-8G.

Two containers 218, such as, but without intending to limit the invention, bottles, vials or ampoules containing predefined dosages and/or concentrations of therapeutic liquid substances that are required in treating a patient, are positioned in container connectors 216. These containers 218 may be single-use containers. Container connectors 216 may be removably attachable and they may be single-use connectors. Container connectors 216 may be connected by luer locks 214 to liquid conduits 215 that lead to assembly base 210.

In some embodiments, there may be valves, such as stopcock valves 224, positioned between container connectors 216 and luer locks 214. In other embodiments (not shown), there may be valves, such as stopcock valves 224, positioned between luer locks 214 and liquid conduits 215. It should be appreciated by persons skilled in the art that valves other than stopcock valves may also be used.

While luer locks generally are indicated throughout the discussion herein, it should readily be understood that other suitable connection fittings known to persons skilled in the art may also be used. In the claims, this element will generally be noted as "connection fittings" or "connection fitting". Such designation is intended to include inter alia luer locks.

Assembly base 210, luer locks 214, stopcock valves 224, containers 218, container connectors 216, and liquid conduits 215 are typically, but with intending to limit the invention, made of rigid plastic. Housing portion 212 may also be formed of a rigid plastic. The exact plastics to be used for these elements are readily selectable by persons skilled in the art.

A side of assembly base 210 is disposed adjacent to device housing portion 212 and is shaped to conform to the adjacent side of housing portion 212. Assembly base 210 may be ultravioletly or ultrasonically bonded to housing portion 212. Alternatively, other methods of attachment known to persons skilled in the art suitable for use with plastics, such as adhesive gluing, may also be used.

Alternatively, in other embodiments, assembly base 210, luer lock 214, liquid conduit 215, stopcock valve 224 and container connector 216 may be constructed as an integral unit with handpiece housing portion 212 by using, for example, injection molding.

Container connectors 216, luer locks 214, liquid conduits 215, stopcock valves 224 and assembly base 210 collectively define, and will be herein referred to as a "therapeutic substance supply assembly" 290.

In some embodiments, such as the one discussed in conjunction with FIGS. 8D-8E below, there may be no need for stopcock valves. In such cases, the term "therapeutic substance supply assembly" 290 will be defined as previously but without the inclusion of stopcock or other valves.

More generally, a therapeutic substance supply assembly 290 is a structure attachable to a housing portion, such as element 212, including a container connector, such as element 216, for receiving a container, such as container 218. The structure allows container 218 to be in fluid flow communication with liquid discharge nozzles, such as discharge nozzles 222, of a nozzle arrangement, such as arrangement 220.

It should be understood that the specific design of the therapeutic substance supply assemblies 290 shown in FIGS. 8A-8C and FIGS. 8D-8G are exemplary only. Other designs may be used if they perform the functions of the assembly 290 as discussed herein.

Assembly base 210 is constructed and configured to fulfill two functions. First, it is configured to allow mounting of the therapeutic substance supply assembly 290 on housing portion 212. Second, assembly base 210 is formed with a conduit (242 in FIG. 8F), herein often denoted as an "assembly base conduit", allowing fluid flow communication between therapeutic substance supply assembly 290 and liquid inlet port 209 (discussed below) via flexible tube 230.

In many embodiments, container connector 216 may be a separate adaptor-like element screwable into, or otherwise removably positionable in, a conduit so that container 218, when positioned in connector 216, is in fluid flow communication with liquid conduits 215 and assembly base 210.

The therapeutic substances in containers 218 are conveyed through container connectors 216 either under gravity or as a result of the therapeutic substances in container 218 being provided under pressure. A puncturing element 217 as shown in FIG. 8F may be present in container connector 216. The puncturing element 217 can puncture a cap 219 (also best seen in FIG. 8F) of container 218 allowing the therapeutic substance to flow out of container 218 and ultimately into hand piece housing portion 212, as described below.

Stopcock valves 224 may be operated by the user to control flow of the therapeutic substance from containers 218 into housing portion 212. The operator may, by opening or closing stopcock valves 224, allow the therapeutic materials in one or both of therapeutic substance containers 218 to enter housing portion 212 and exit from nozzle arrangement 220 through liquid discharge nozzle(s) 222 (similar to elements 116 and 154 in, for example, FIGS. 4 and 7, respectively) at distal end 206 of device 200. The therapeutic liquid solution is then accelerated by pressurized gas exiting from gas discharge nozzles (similar to elements 114 and 152 in, for example, FIGS. 4 and 7, respectively) as discussed previously in conjunction with FIGS. 1-7.

The liquid therapeutic materials from containers 218 enter housing portion 212 of device 200 through liquid inlet port 209, the latter discussed in the paragraph immediately below. Liquid conduits 215 and the conduit formed in assembly base 210 (i.e. assembly base conduit-not shown) are in fluid flow communication with liquid inlet port 209. The liquid materials flow from the conduit formed in assembly base 210 (i.e. the assembly base conduit 242 in FIG. 8F) through a flexible plastic tube 230 to port 209. From there, the liquid is transported either via flexible plastic tube 230 or liquid communication tube 118 (FIGS. 2 and 3) through housing portion 212 to discharge nozzle(s) 222 of nozzle arrangement 220.

A gas inlet port 208 and a liquid inlet port 209 are shown at the proximal end 204 of device 200. Gas and liquid are introduced into device 200 through these ports from appropriate gas sources (not shown) and liquid sources (such as containers 218) as described above. The gas may be selected from air, oxygen, nitrogen and carbon dioxide but other non-reactive gases may also be used.

It should readily be understood by persons skilled in the art that the flow of a therapeutic substance from a container 218 positioned in a container connector 216 of a therapeutic substance supply assembly 290 to nozzle arrangement 220 can occur using any suitable fluid flow communication design.

Figure 8D:
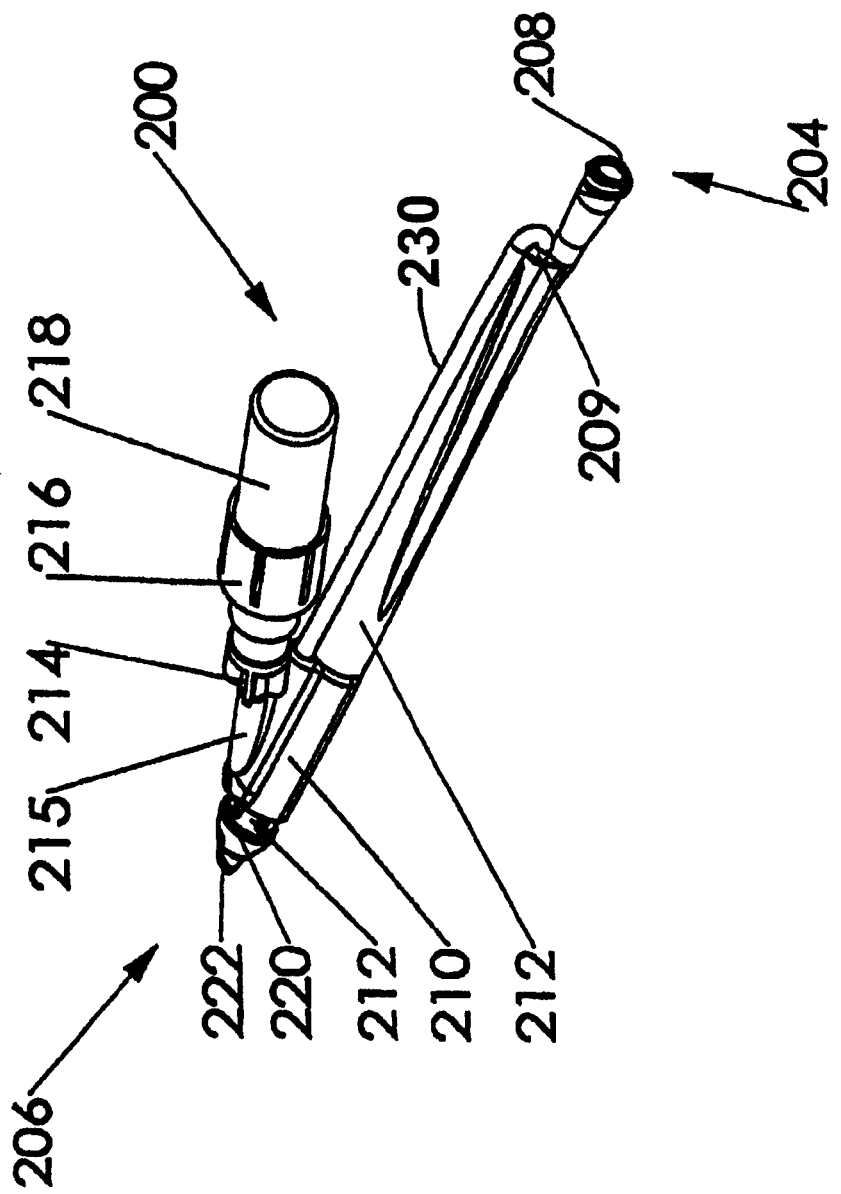
FIGS. 8D-8E are perspective and side views, respectively, of another device for administering therapeutic substances to tissue, constructed and operative substantially in accordance with the embodiment of the present invention shown in FIGS. 8A-8C.
Figure 8E:
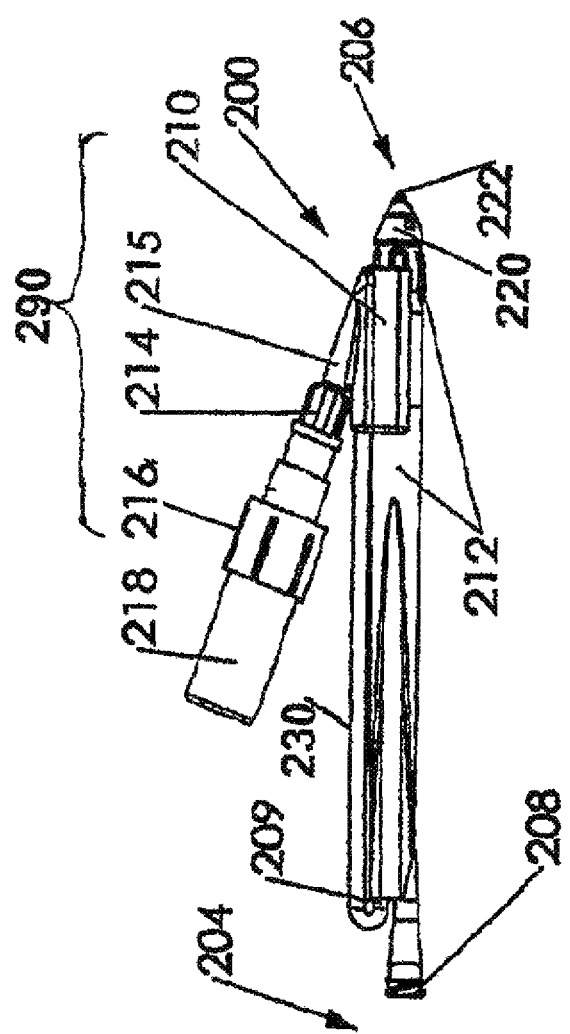
Figure 8F:
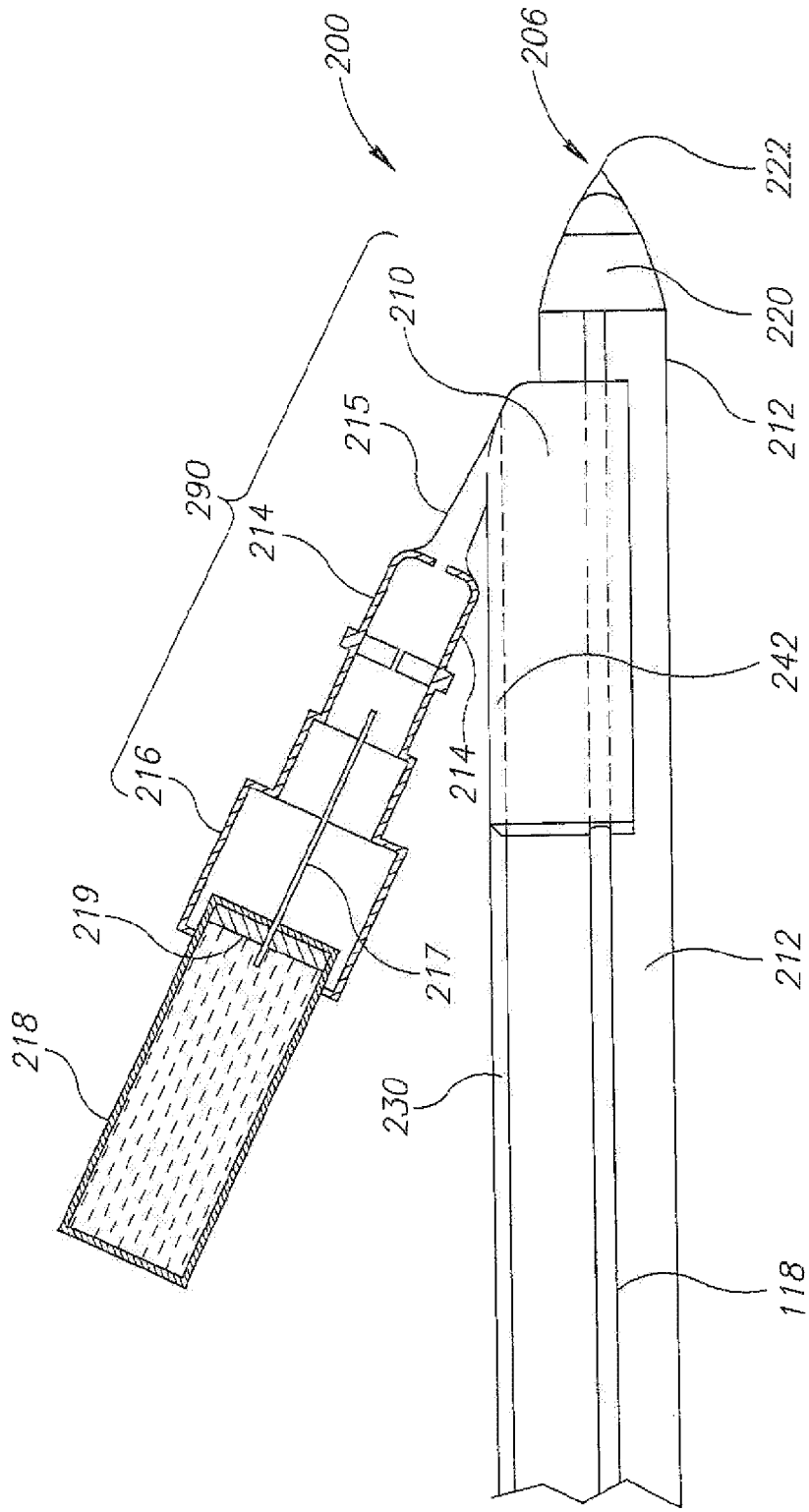
FIG. 8F is a cut away side view of the therapeutic substance supply assembly in FIGS. 8A-8E.
Figure 8G:
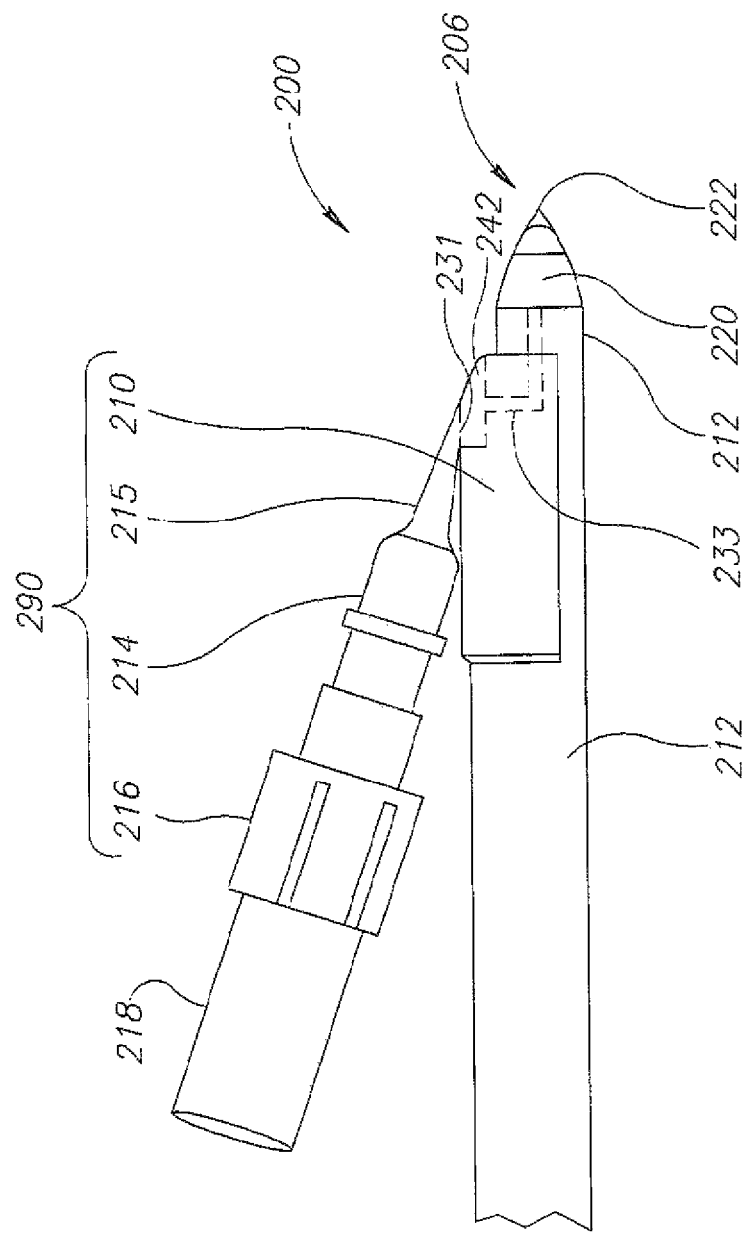
FIG. 8G is a side view of a second embodiment of the present invention.

As an exemplary alternate design as a side view in FIG. 8G, to which reference is now made, housing portion 212 may be formed with an aperture 231 on its long tubular side intended for presentation to, and for fluid communication with, assembly base 210 of therapeutic substance supply assembly 290. The assembly base conduit 242 within assembly base 210, shown in FIG. 8G, is in this design formed so that it may be brought into fluid flow communication and general registration with the aperture 231 situated on housing portion 212.

A tube 233 equivalent to liquid communication tube 118 (the latter best seen in FIG. 2) of housing portion 212 is adapted so that it is in fluid flow communication with therapeutic substance supply assembly 290 via the above described aperture 231 and the conduit formed in assembly base 210 (i.e. assembly base conduit 242). At least one liquid discharge nozzle 222 substantially equivalent in construction and operation to liquid discharge nozzle 116 of FIGS. 2 and 4, receives the liquid therapeutic substance from the assembly base conduit 242 after it has passed through the aperture 231 and liquid communication tube 233, the latter the equivalent of liquid communication tube 118 formed in housing 212. The liquid is then discharged from liquid discharge nozzle(s) 222 in nozzle arrangement 220 (FIGS. 8A-8G).

In this design, no transmission tube 230 and no liquid inlet port 209 are required. In this design, an adhesive, such as a silicon adhesive, which is used to connect therapeutic substance supply assembly 290 to housing portion 212 may also function as a sealant preventing loss of liquid during its transfer from containers 28 through assembly base 210 into housing portion 212, via aperture 231 and liquid communication tube 233.

FIGS. 8D and 8E show a device 200 similar to device 200 in FIGS. 8A-8C but having only a single therapeutic substance supply assembly 290. Elements in 8D-8E are similar to ones in FIGS. 8A-8C and have been numbered similarly. All elements in FIGS. 8D-8E are constructed and operated as discussed in conjunction with FIGS. 8A-8C and therefore will not be described again. In FIGS. 8D-8E, no stopcock valve is present. In other embodiments of FIGS. 8D-8E, valves, such as, but not limited to, stopcock valves, may be added.

It should readily be evident to one skilled in the art that devices, such as device 200, may also be configured to operate with more than two therapeutic substance container connectors 216 and/or more than two therapeutic substance supply assemblies.

Devices 200 discussed in conjunction with FIGS. 8A-8G may be ergonomically designed and balanced for easier one-hand use by an operator.

Devices 200 may be used to apply the therapeutic droplet stream either topically or subcutaneously.

Devices 200 may also be constructed to have a multiple nozzle configuration, similar to, for example, the one shown in and discussed hereinabove in conjunction with FIG. 7.

Because many therapeutic substances have a reduced shelf life after their original container has been opened, use of throw-away single-use therapeutic solution containers 218 obviates many difficulties readily apparent to persons skilled in the art. Moreover, since the containers to be used may be selected from among containers that may contain a wide variety of therapeutic substances each being manufactured at different quantities and/or concentrations, the use of such containers is an advantage. Finally, the positioning of therapeutic containers 218 directly on operating devices 200 allows for ease of use of devices 200 by reducing the need for restricting tubing and conduits. Devices 200 therefore are more easily adapted for single hand use by the user.

It will be appreciated by persons skilled in the art that the present invention is not limited by the drawings and description hereinabove presented. Rather, the invention is defined solely by the claims that follow.

The invention claimed is:
1. A device for administering a therapeutic substance to tissue for use with a pressurized gas source, and comprising:
 a) a housing having a liquid inlet port;
 b) a gas inlet port connected to the pressurized gas source;
 c) at least one therapeutic substance supply assembly mounted onto said housing, each therapeutic substance supply assembly comprising at least one container connector configured for receiving a container containing a predefined quantity or concentration of a liquid therapeutic substance, each container in fluid flow communication with one of at least one valve projecting from and external to said assembly, each of said at least one valve is associated with a different container and user operable between an open and a closed position, said at least one valve is adapted for control of a continuous flow of said at least one liquid therapeutic substance during operation of said device; and d) a stream jet delivery nozzle arrangement in fluid flow communication with said gas inlet port and in fluid flow communication with said therapeutic substance supply assembly, the liquid therapeutic substance being discharged from said stream jet delivery nozzle arrangement into an elevated velocity flow of gas discharged from said delivery nozzle arrangement, wherein the liquid therapeutic substance is brought from an assembly base of said therapeutic substance supply assembly to said liquid inlet port through a flexible tube positioned external to said housing which directly connects said assembly base to said liquid inlet port.

2. A device according to claim 1, wherein said therapeutic substance supply assembly further comprises at least one liquid conduit, said at least one container connector of said therapeutic substance supply assembly in liquid supply communication with said at least one liquid conduit and with said assembly base.

3. A device according to claim 1, wherein said assembly base is an at least partially hollow integral mounting and connector member for mounting said therapeutic substance supply assembly onto said housing, further having a conduit formed in the assembly base in fluid flow communication with an at least one liquid conduit of said assembly and said liquid inlet port for facilitating fluid flow therebetween.

4. A device according to claim 1 wherein said at least one container connector comprises a puncturing element for piercing a cap of the container containing a liquid therapeutic substance thereby allowing the therapeutic substance to flow from the container either under pressure when the therapeutic substance is packaged in the container under pressure or by gravity.

5. A device according to claim 1, wherein said liquid inlet port is in fluid flow communication with said therapeutic substance supply assembly and also in fluid flow communication with said stream jet delivery nozzle arrangement.

6. A device according to claim 1 further comprising at least one valve positioned on said therapeutic substance supply assembly for controlling fluid flow therethrough.

7. A device according to claim 1, wherein said assembly base is an at least partially hollow integral mounting and connector member for mounting said therapeutic substance supply assembly onto said housing.

8. A device according to claim 1, wherein said therapeutic substance supply assembly further comprises a connection fitting, said connection fitting in fluid flow communication with said at least one container connector, an at least one liquid conduit and said assembly base.

9. A device according to claim 1, wherein said therapeutic substance supply assembly further comprises a connection fitting, a liquid conduit and said assembly base.

10. A device according to claim 1 wherein said at least one therapeutic substance supply assembly comprises at least two container connectors.

11. A device according to claim 1, where said at least one valve is a stopcock valve.

12. A device according to claim 1 wherein said valve controls liquid flow without mixing the liquid therapeutic substance with a gas from said pressurized gas source.

13. A system for administering a therapeutic substance to tissue, which comprises:
a) a pressurized gas source;
b) at least one container containing a predefined quantity or concentration of a liquid therapeutic substance; and
c) a device which comprises:
(i) a housing having a liquid inlet port;
(ii) a gas inlet port connected to said pressurized gas source;
(iii) at least one therapeutic substance supply assembly mounted onto said housing, each therapeutic substance supply assembly comprising at least one container connector configured for receiving a container of the at least one container containing a predefined quantity or concentration of a liquid therapeutic substance, each container in fluid flow communication with one of at least one valve projecting from and external to said assembly, each of said at least one valve is associated with a different container and user operable between an open and a closed position, said at least one valve is adapted for control of a continuous flow of said at least one liquid therapeutic substance during operation of said device; and
(iv) a stream jet delivery nozzle arrangement in fluid flow communication with said gas inlet port and in fluid flow communication with said therapeutic substance supply assembly, the liquid therapeutic substance being discharged from said stream jet delivery nozzle arrangement into an elevated velocity flow of gas discharged from said delivery nozzle arrangement, wherein said at least one valve projecting from and external to said assembly is configured for direct immediate user accessibility.

14. A system according to claim 13 wherein the liquid therapeutic substance is brought to said liquid inlet port from said therapeutic substance supply assembly through a flexible tube in fluid flow communication with said assembly base, said flexible tube positioned external to said housing.

15. A system according to claim 13, wherein said at least one container connector comprises a puncturing element for piercing a cap of said at least one container of the liquid therapeutic substance thereby allowing the therapeutic substance to flow from said at least one container either by gravity or under pressure when the therapeutic substance is packaged in the container under pressure.

16. A system according to claim 13, wherein said liquid inlet port is in fluid flow communication with said therapeutic substance supply assembly and also in fluid flow communication with said stream jet delivery nozzle arrangement.

17. A system according to claim 13, wherein said housing has a long tubular side having an aperture formed therein and further includes a liquid communication tube within said housing extending from said aperture and in fluid flow communication with at least one liquid discharge nozzle.

18. A system according to claim 13 wherein said at least one therapeutic substance supply assembly comprises at least two container connectors.

19. A system according to claim 13, where said at least one valve is a stopcock valve.

20. A system according to claim 13 wherein said valve controls liquid flow without mixing the liquid therapeutic substance with a gas from said pressurized gas source.

21. A system for administering a therapeutic substance to tissue, which comprises:
a) a pressurized gas source;
b) at least one container containing a predefined quantity or concentration of a liquid therapeutic substance; and
c) a device which comprises:
(i) a housing having a liquid inlet port;
(ii) a gas inlet port connected to said pressurized gas source;

(iii) at least one therapeutic substance supply assembly mounted onto said housing, each therapeutic substance supply assembly comprising at least one container connector configured for receiving a container of the at least one container containing a predefined quantity or concentration of a liquid therapeutic substance, each container in fluid flow communication with one of at least one valve projecting from and external to said assembly, each of said at least one valve is associated with a different container and user operable between an open and a closed position, said at least one valve is adapted for control of a continuous flow of said at least one liquid therapeutic substance during operation of said device, and where said valve does not mix said therapeutic substance liquid with said pressurized gas; and (iv) a stream jet delivery nozzle arrangement in fluid flow communication with said gas inlet port and in fluid flow communication with said therapeutic substance supply assembly, the liquid therapeutic substance being discharged from said stream jet delivery nozzle arrangement into an elevated velocity flow of gas discharged from said delivery nozzle arrangement.

* * * * *